US00PP17054P2

(12) United States Plant Patent
Friday

(10) Patent No.: US PP17,054 P2
(45) Date of Patent: Aug. 22, 2006

(54) PEACH TREE NAMED 'P.F. 11 PEACH'

(50) Latin Name: *Prunus persica*
Varietal Denomination: P.F. 11 Peach

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/980,842

(22) Filed: Nov. 4, 2004

(51) Int. Cl.
*A01H 5/00* (2006.01)

(52) U.S. Cl. ..... Plt./198
(58) Field of Classification Search ..... Plt./198
See application file for complete search history.

(56) References Cited

U.S. PATENT DOCUMENTS

PP9,859 P * 4/1997 Zaiger et al. ..... Plt./186
PP15,498 P2 * 1/2005 Friday ..... Plt./198

OTHER PUBLICATIONS http://www.flaminfury.com/?action=147 Paul Friday's Flamin' Fury Peaches Testimonials.*
http://www.flaminfury.com/?action=149 Paul Friday's Flamin' Fury Peaches Flamin' Fury Varieties.*

* cited by examiner

*Primary Examiner*—Wendy Haas

(57) ABSTRACT

A new and distinct variety of peach tree having the following unique combination of desirable features:

1. Producing a very firm fruit having a resilient flesh texture.
2. Blossoms are non-showy when in full bloom.
3. A substantially spheriodal fruit with yellow flesh having red mottling.
4. Early maturing fruit of good taste.
5. A mid-season peach variety which matures with Redhaven and which has good storage and shelf life.
6. A stone having an arcuate base.

1 Drawing Sheet

Botanical classification: *Prunus persica.*
Variety denomination: 'P.F. 11 Peach'.

ORIGIN OF VARIETY

The new peach tree (hereinafter referred to as the 'P.F. 11 Peach' peach tree) was originated by Paul Friday in an experimental orchard, which is maintained for the purposes of breeding peach trees, located in Coloma, Mich. Coloma is located in the southwest section of Michigan, USDA Hardiness Zone 6a, with observed temperature ranges of minus 12 degree Fahrenheit to 90 degree Fahrenheit, also with annual rainfall of about 40 inches.

In an ongoing mass selection breeding program, unpatented superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. 11 Peach', was a selection from one such unpatented seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard located in Coloma, Mich. The asexual propagation demonstrates that such reproductions of the characteristics of the tree are consistent and are established and transmitted through succeeding propagation.

SUMMARY OF THE VARIETY

The new and distinct variety of peach tree is of moderate upright growth and a regular and productive bearer of peaches. The blossoms are characterized by being contracted or partially spread when in full bloom.

The blossoms of the present peach tree at full bloom may be characterized as being non-showy; i.e., angularly spaced five blossom petal projecting upwardly at an inclined angle so as to form a blossom, having a diameter of about 1" measured across the blossoms. The typical non-showy blossoms as exemplified for example by the 'Redhaven' (unpatented) peach has five (5) radially extending and angularly spaced petals projecting upwardly at a relatively steep inclined angle so that the diametrical measurement across the outer edges of the petals is about ½".

The flesh of the fruit of the present peach tree is firm and is yellow with some red mottling in the flesh.

The skin is smooth and is of dark red color over about eighty (80%) percent of its surface at maturity. The red color occurs over about sixty (60%) percent of the surface about 10 days prior to maturity. At maturity the peach is substantially spheroidal with the diameter ranging between about 2½" to 3 inches.

It is noteworthy that the fruit of this tree is further characterized as having smooth, gently rounded cheeks at the blossom end of the fruit. These protrude to form fruit surfaces higher than the blossom point. This characteristic reduces fruit damage in harvest, shipping and storage, by reducing the exposure of and damage to the apical blossom protrusion in handling. Thus breaching of the skin and formation of an entry point for microorganisms which cause rot in many other commercially important peach varieties harvested in the same production period is reduced in this fruit.

The fruit has a firm flesh and may be described as resilient to the extent that the flesh is yieldable and restorable to its original state when subjected to impact forces which may cause permanent deformities in peaches of commercial varieties. The firmness of the fruit facilitates handling and packaging of the peaches without damaging the same for shipment. This results in less spoilage and also increases the shelf life.

The fruit matures in the middle part of the peach-growing season of Southwestern Michigan. The fruit as mentioned heretofore is of red color over about eighty (80%) percent of its spherodial surface and has a very attractive appearance.

BRIEF DESCRIPTION OF THE PHOTOGRAPHS

The accompanying photographic illustrations of an 11 year old tree of the new variety show the following:

The top photograph depicts three well-rounded fruit showing an unpronounced suture. One specimen of the fruit is bisected at a ninety-degree angle to the plane of the suture with the stone retained in half showing its freestone characteristic and a clear yellow flesh and a minimum of red in the pit cavity. A tape measure is present indicating the large size of the fruit.

The bottom photograph depicts leaves of medium length and width, having notably very fine serrated margins. A tape measure is present, demonstrating the medium size of the leaves.

DESCRIPTION OF VARIETY

The detailed botanical description of the foliage and fruit of the new variety of peach tree of 11 years old and grown in its own roots is based upon observations of the specimens grown at Coloma, Mich. with the color terminology other than the terminology expressed in common terms, in accordance with the Pantone Matching System (PMS) as used internationally to identify printed colors.

Botanical classification: *Prunus persica* cultivar 'P.F. 11 Peach'.

Tree:
- *Age.*—Eleven (11) years.
- *Height.*—Unpruned 13'.
- *Width.*—Unpruned 16'.
- *Size.*—Medium.
- *Vigor.*—Medium.
- *Density.*—Medium, pruning required.
- *Form.*—Spreading.
- *Production.*—Very good, requires thinning — Produces 1½ Bu per tree per year.
- *Bearer.*—Good.
- *Disease resistance to bacterial leaf and fruit spot.*—Very resistant.
- *Rootstock.*—Grown in its own roots.

Trunk:
- *Bark color.*—Gray (pantone # 424).
- *Size.*—Medium.
- *Surface.*—Rough.
- *Diameter.*—5¼" at 18" above ground.
- *Lenticels.*—Pronounced.
- *Lenticels color.*—Light brown (pantone # 155).
- *Lenticels size.*—⅛" to 3/16".

Branches:
- *Size.*—Medium 2⅛" diameter at 5" from trunk union.
- *Surface.*—Semi-smooth.
- *Branch color.*—Gray (pantone # 422).
- *Lenticels per square inch on branch.*—Five (5).
- *Lenticels size.*—⅛".
- *Lenticels color.*—Reddish brown (pantone # 157).
- *Crotch angles.*—Natural right angles.
- *Internodes length.*—½".

Leaves:
- *Size.*—Average length 7⅛" — average width 1¾".
- *Form.*—Lanceolate — pointed.
- *Thickness.*—Medium.
- *Texture.*—Glabrous.
- *Margin.*—Very mild serrated — not pronounced.
- *Leaf base shape.*—Acute.
- *Leaf apex shape.*—Pointed.
- *Petiole length.*—⅝".
- *Gland number.*—2 to 3 on each side of petiole — (notably located on the petiole).
- *Gland color.*—Tan to brown in fall.
- *Gland shape.*—Almost flat with limited dishing.
- *Leaf color.*—Top of leaf dark green (pantone # 357) bottom of leaf green (pantone # 364).

Flower buds:
- *Size.*—½" long — ⅜" wide.
- *Shape.*—Ovoid.
- *Color.*—Dark pink (pantone # 225).

Flowers:
- *Blooming period.*—Apr. 16, 2004 to Apr. 24, 2004.
- *Bloom size.*—1" diameter.
- *Bloom depth.*—⅝" deep.
- *Shape of petals.*—Ovate.
- *Petal margin.*—Smooth (entire).
- *Petal base shape.*—Flat to Rounded.
- *Petal apex shape.*—Rounded.
- *Size of petal.*—½" long — ¼" wide.
- *Number of petals.*—Five (5).
- *Petal color.*—Top of petal — Pink (pantone # 230) Bottom of petal — Light pink (pantone # 217).
- *Sepal size.*—¼" long 3/16" wide.
- *Number of sepals.*—Five (5).
- *Sepal shape.*—Slightly cupped (ovate).
- *Sepal color.*—Light green (pantone # 391).
- *Number of anthers.*—Twenty (20).
- *Anthers color.*—Brown (pantone # 168).
- *Number of stamens.*—Twenty (20).
- *Stamen length.*—7/16".
- *Stamen color.*—Pink (pantone # 223).
- *Pistil length.*—½".
- *Pistil color.*—Yellow (pantone # 106).
- *Pollen.*—Present.
- *Flowers per cluster.*—Two (2).
- *Flower and petal color.*—Pink (pantone # 230).
- *Fragrance.*—None.

Fruit:
*Maturity when described.*—Firm ripe.
*Date of first picking.*—Aug. 1, 2004.
*Date of last picking.*—Aug. 9, 2004.
*Size.*—2¾" to 3" diameter.
*Form.*—Spherical.
*Suture.*—Not pronounced — stays firm.
*Weight.*—7.3 oz. to 8 oz.

Skin:
*Thickness.*—Medium as compared to the species.
*Texture.*—Medium as compared to the species.
*Tendency to crack.*—None.
*Down.*—Much shorter than is typical.
*Color.*—Red (pantone # 194) over 85% with a Yellow (pantone # 110) ground color.

Flesh:
*Texture.*—Firm, non-melting free of fiber.
*Ripens.*—Evenly.
*Flavor.*—Excellent.
*Aroma.*—Good.
*Eating quality.*—Very good.
*Brix.*—Average of 13%.
*Color.*—Yellow (pantone # 110).
*Pit cavity color.*—Red (pantone # 194).

Stone:
*Type.*—Freestone.
*Size.*—1½" long.
*Form.*—Ovoid.
*Base.*—Straight.
*Apex.*—Pointed.
*Sides.*—Uneven.
*Surface.*—Furrowed.
*Color.*—Brown (Pantone # 471).
*Tendency to crack.*—None.
*Kernel.*—¾" long, ½" wide, ⅛" thick.
*Kernel taste.*—Slight bitterness.

Use: Dessert.
Shipping quality: Excellent.
Keeping quality: Very Good (up to three (3) weeks).
Disease resistance: The fruit is resistant to brown rot, and bacterial spot.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

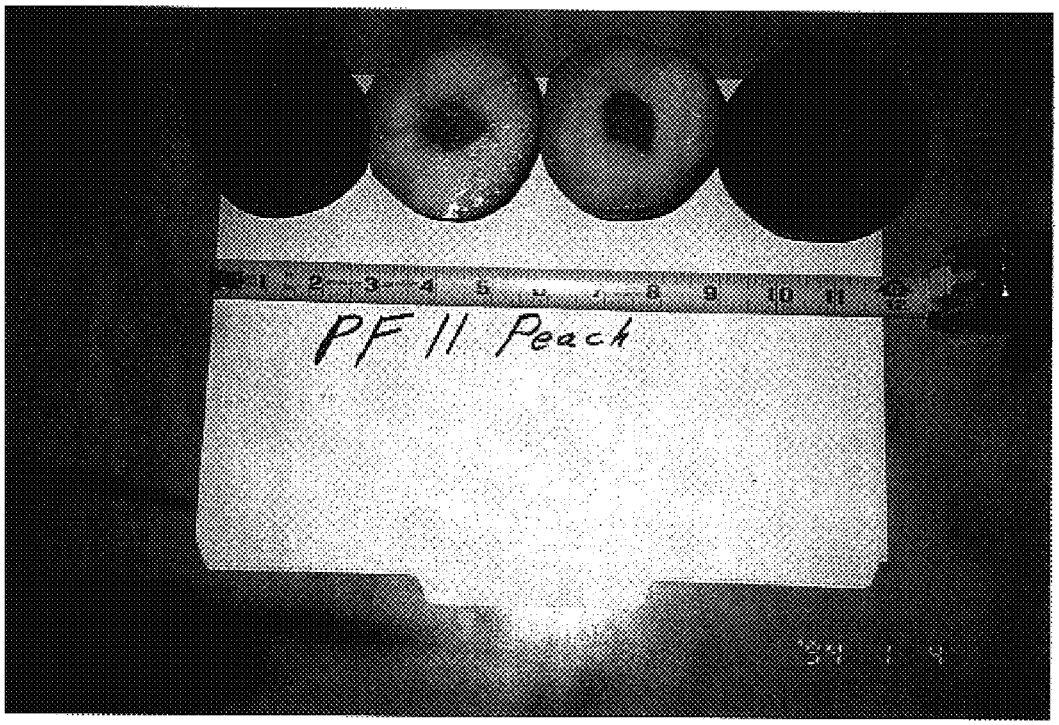
PF 11 Peach
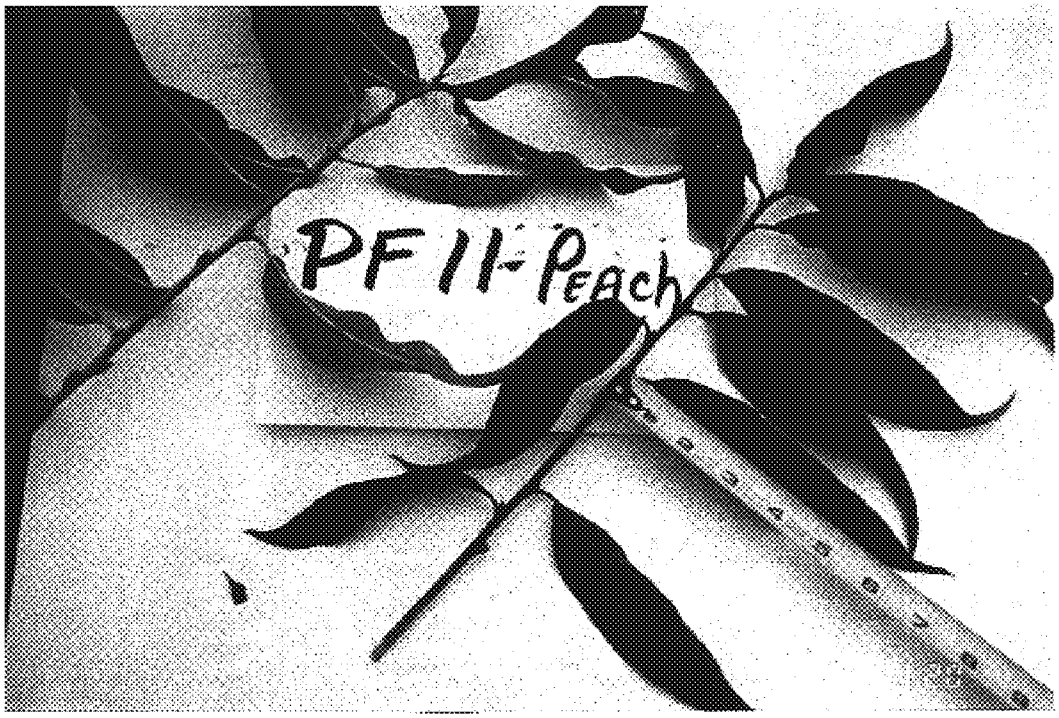
PF 11- Peach